United States Patent [19]

Petersen

[11] Patent Number: 5,563,047
[45] Date of Patent: Oct. 8, 1996

[54] METHOD FOR CROSSLINKING OF HAEMOGLOBIN

[75] Inventor: Bent R. Petersen, København Ø, Denmark

[73] Assignee: Novo Nordisk A/S, Bagsvaerd, Denmark

[21] Appl. No.: 432,172

[22] PCT Filed: Dec. 1, 1993

[86] PCT No.: PCT/DK93/00397

§ 371 Date: May 10, 1995

§ 102(e) Date: May 10, 1995

[87] PCT Pub. No.: WO94/14460

PCT Pub. Date: Jul. 7, 1994

[30]  Foreign Application Priority Data

Dec. 3, 1992 [DK] Denmark .................................. 1450/92

[51] Int. Cl.$^6$ ............................. C12P 21/00; C12N 9/10
[52] U.S. Cl. ............................. 435/68.1; 435/193; 514/6; 530/385
[58] Field of Search ................. 435/193, 68.1; 514/6; 530/385

[56]     References Cited

U.S. PATENT DOCUMENTS

| 4,001,200 | 1/1977 | Bonsen et al. | 530/385 |
|---|---|---|---|
| 4,529,719 | 7/1985 | Tye | 514/6 |
| 4,777,244 | 10/1988 | Bonhard | 530/385 |
| 5,128,452 | 7/1992 | Hai et al. | 530/385 |
| 5,156,956 | 10/1992 | Motoki et al. | 435/68.1 |
| 5,279,839 | 1/1994 | Gottmann et al. | 426/20 |
| 5,330,778 | 7/1994 | Stark et al. | 426/531 |
| 5,399,671 | 3/1995 | Kluger et al. | 530/385 |
| 5,409,731 | 4/1995 | Nakagawa et al. | 427/2.12 |
| 5,455,158 | 10/1995 | Vogel et al. | 435/7.21 |

FOREIGN PATENT DOCUMENTS

| 4126039 | 4/1992 | Japan . |
|---|---|---|
| WO92/03153 | 3/1992 | WIPO . |

*Primary Examiner*—Herbert J. Lilling
*Attorney, Agent, or Firm*—Steve T. Zelson, Esq.; Elias J. Lambiris, Esq.

[57]        ABSTRACT

Haemoglobin is crosslinked by means of transglutaminase, whereafter the transglutaminase is inactivated. The crosslinked haemoglobin can be used as a molecular agent for oxygen transportation, as an oxygen scavenger, and as a constituent of a food composition.

4 Claims, 1 Drawing Sheet

METHOD FOR CROSSLINKING OF HAEMOGLOBIN

The invention comprises a method for crosslinking of haemoglobin and a use of such crosslinked haemoglobin.

From Biotechnology of Blood, edited by Jack Goldstein, 1991, page 108, first full paragraph it appears that the prior art methods for polymerisation of haemoglobin are associated with several drawbacks, especially the heterogenous distribution of polymers due to the unspecificity of the hitherto used crosslinking agents and the fact that the degree of polymerisation is difficult to control.

Thus, it is the purpose of the invention to provide a method for crosslinking of haemoglobin, in regard to which the crosslinked haemoglobin exhibits a more homogenous distribution of polymers and a better controllable degree of polymer, and a use of such crosslinked haemoglobin.

The method according to the invention for crosslinking of haemoglobin is characterized by the fact that haemoglobin present in an aqueous solution thereof with a pH between 5 and 9 is crosslinked by means of transglutaminase (EC 2.3.2.13), whereafter the crosslinking is stopped at the wanted degree of polymerisation.

Surprisingly it has been found that transglutaminase is a very specific crosslinking agent, and that it is possible to obtain a very good controllable degree of polymerisation by means of the method according to the invention.

A preferred embodiment of the method according to the invention is characterized by the fact that the pH value of the aqueous solution is between 6.5 and 8. The crosslinking reaction proceeds with a most satisfactory velocity in this pH interval.

A preferred embodiment of the method according to the invention is characterized by the fact that the maximum amount of transglutaminase is 2% of pure transglutaminase protein, calculated in regard to the haemoglobin protein. Higher levels of transglutaminase than 2% will prove to be uneconomic. Even at very low levels below 2% the crosslinking will proceed, if given the time.

A preferred embodiment of the method according to the invention is characterized by the fact that the crosslinking is stopped by heat inactivation of the transglutaminase, preferably by heating to up to 65° C. for 5 minutes. This is the most simple and effective way of inactivation.

Also, the invention comprises a use of the crosslinked haemoglobin producible by means of the method according to the invention, due to any of the inherent properties of the crosslinked haemoglobin.

A preferred embodiment of the use of the crosslinked haemoglobin producible by means of the method according to the invention is as a molecular agent for oxygen transportation, i.e. as a blood substitute. The desirability of new blood substitutes are well known, vide Biotechnology of Blood, edited by Jack Goldstein, 1991, page 101. It has been found that it is easy to produce the crosslinked haemoglobin according to the invention with a molecular weight well above 64,000 Dalton, which is above the cut-off value of the kidneys, 60,000 Dalton. This is one of the conditions for a satisfactory blood substitute.

A preferred embodiment of the use of the crosslinked haemoglobin producible by means of the method according to the invention is as an oxygen scavenger. It has been found that this haemoglobin functions effectively as an oxygen scavenger, e.g. in food items, and that addition of antioxidants hereby can be eliminated or reduced.

A preferred embodiment of the use of the crosslinked haemoglobin producible by means of the method according to the invention is as a constituent of a food composition.

EXAMPLE 1

Figure 1:
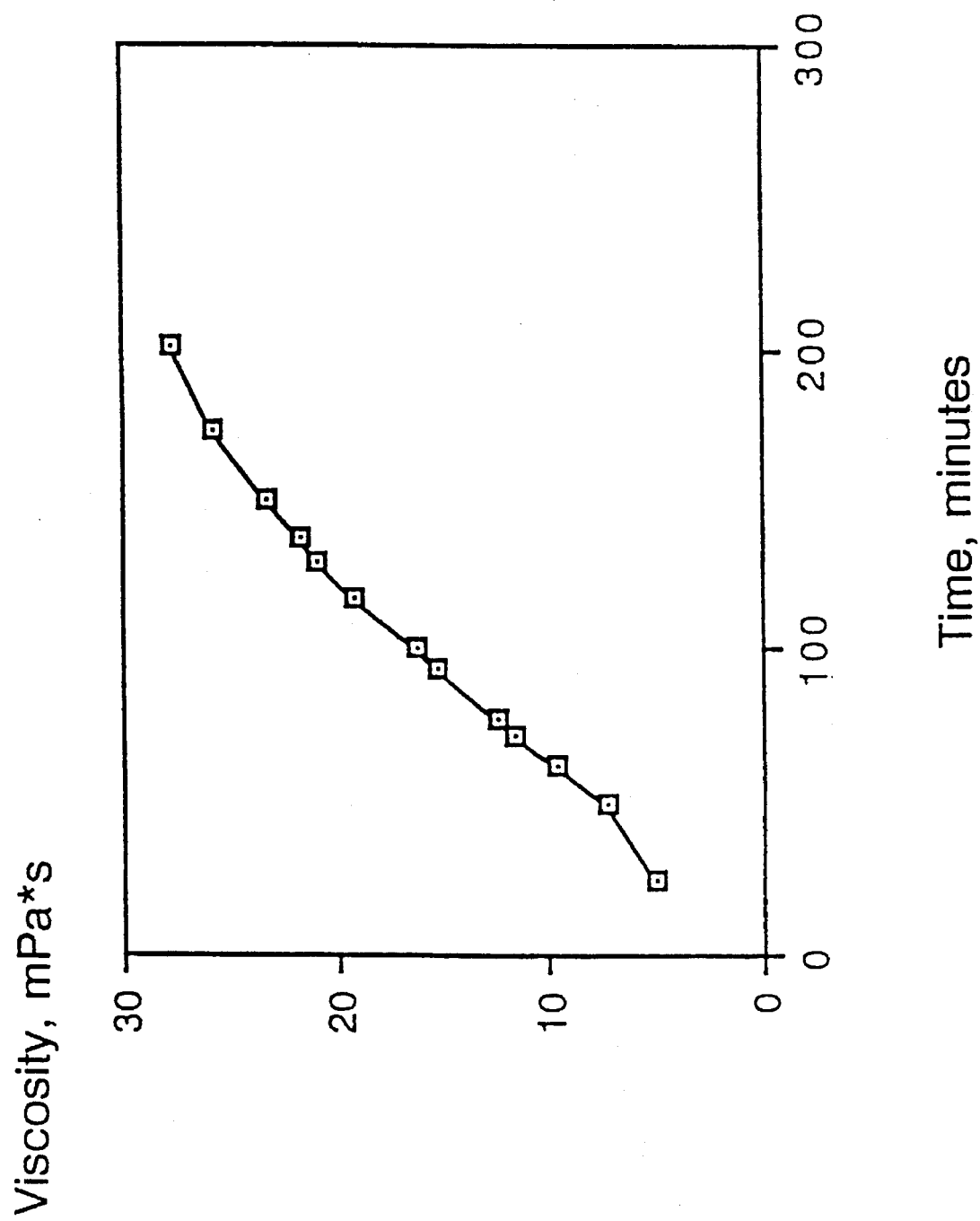
FIG. 1 demonstrates the increase in viscosity with time for the polymerization of haemoglobin with transglutaminase.

To 200 g of a 14% solution (w/w) of haemoglobin (Merck, Darmstadt, BRD) (pH 7.0, temperature 37° C.) with a concentration of $Ca^{++}$ of 5 mM transglutaminase was added in an amount of 0.4% (w/w) in relation to the amount of haemoglobin, i.e. 112 mg. The transglutaminase was produced as indicated in Example 1 of WO 93/15234. The reaction was carried out for 200 minutes, and subsequently the activity of the transglutaminase was inactivated by heating to 65° C. for 5 minutes. Reference is made to FIG. 1, which shows the progression of the polymerization expressed as viscosity. The crosslinked haemoglobin was isolated by lyophilization.

I claim:

1. A method for crosslinking a hemoglobin, comprising
   (a) treating an aqueous solution which comprises the hemoglobin with a transglutaminase wherein the aqueous solution has a pH between 5 and 9; and
   (b) inactivating the transglutaminase at a desired degree of polymerization.

2. The method according to claim 1, wherein the aqueous solution has a pH between 6.5 and 8.

3. The method according to claim 1, wherein the maximum amount of the transglutaminase is 2% of pure transglutaminase protein, calculated in regard to the haemoglobin protein.

4. The method according to claim 1, wherein the transglutaminase is inactivated by heating to up to 65° C. for 5 minutes.

* * * * *